United States Patent
Courtine et al.

(10) Patent No.: US 10,632,105 B2
(45) Date of Patent: Apr. 28, 2020

(54) PHARMACOLOGICAL STIMULATION TO FACILITATE AND RESTORE STANDING AND WALKING FUNCTIONS IN SPINAL CORD MOTOR DISORDERS

(71) Applicant: ECOLE POLYTECHNIQUE FEDERALE DE LAUSANNE (EPFL), Lausanne (CH)

(72) Inventors: Grégoire Courtine, Lausanne (CH); Quentin Barraud, Vevey (CH); Pavel Musienko, St. Petersburg (RU)

(73) Assignee: ÉCOLE POLYTECHNIQUE FÉDÉRALE DE LAUSANNE (EPFL), Lausanne (CH)

(*) Notice: Subject to any disclaimer, the term of this patent is extended or adjusted under 35 U.S.C. 154(b) by 174 days.

(21) Appl. No.: 14/902,556

(22) PCT Filed: Jun. 27, 2014

(86) PCT No.: PCT/EP2014/063654
§ 371 (c)(1),
(2) Date: Dec. 31, 2015

(87) PCT Pub. No.: WO2015/000800
PCT Pub. Date: Jan. 8, 2015

(65) Prior Publication Data
US 2016/0158204 A1    Jun. 9, 2016

(30) Foreign Application Priority Data

Jul. 1, 2013 (EP) ..................................... 13174477

(51) Int. Cl.
| | | |
|---|---|---|
| *A61K 31/421* | (2006.01) | |
| *A61K 31/4164* | (2006.01) | |
| *A61K 31/4168* | (2006.01) | |
| *A61K 31/4178* | (2006.01) | |
| *A61K 9/00* | (2006.01) | |
| *A61N 1/05* | (2006.01) | |
| *A61N 1/36* | (2006.01) | |
| *A61K 45/06* | (2006.01) | |
| *A61K 31/136* | (2006.01) | |

(52) U.S. Cl.
CPC .......... *A61K 31/421* (2013.01); *A61K 9/0019* (2013.01); *A61K 31/136* (2013.01); *A61K 31/4164* (2013.01); *A61K 31/4168* (2013.01); *A61K 31/4178* (2013.01); *A61K 45/06* (2013.01); *A61N 1/0551* (2013.01); *A61N 1/36003* (2013.01)

(58) Field of Classification Search
CPC ............ A61K 31/4178; A61K 31/4164; A61K 31/4168; A61K 31/421
See application file for complete search history.

(56) References Cited

U.S. PATENT DOCUMENTS

| | | | | |
|---|---|---|---|---|
| 4,742,054 A | * | 5/1988 | Naftchi | A61K 31/415 424/449 |
| 5,958,933 A | * | 9/1999 | Naftchi | A61K 31/4164 514/245 |
| 6,281,207 B1 | * | 8/2001 | Richter | A61K 31/55 514/214.02 |
| 7,135,497 B1 | | 11/2006 | Zeman et al. | |
| 8,063,087 B2 | * | 11/2011 | Chow | C07D 233/70 514/392 |
| 2003/0113725 A1 | * | 6/2003 | Small | C12Q 1/6883 435/6.11 |
| 2007/0004567 A1 | | 1/2007 | Shetty et al. | |
| 2008/0275129 A1 | * | 11/2008 | Lundstedt | A61K 31/155 514/632 |

FOREIGN PATENT DOCUMENTS

| | | | | | |
|---|---|---|---|---|---|
| WO | WO-9409808 A1 | * | 5/1994 | ........... | A61K 31/435 |
| WO | WO 2006026850 A1 | * | 3/2006 | ........... | A61K 31/473 |
| WO | WO-2006026850 A1 | * | 3/2006 | ........... | A61K 31/473 |

(Continued)

OTHER PUBLICATIONS

Haller et al (Psychopharmacology vol. 134 pp. 107-114, published 1997).*
Paterini et al (Journal of Neuroinflammation vol. 8 pp. 31-45, published 2011).*
Norman et al (Spinal Cord vol. 36, pp. 699-715, published 1998).*
Alphapharm (Mirtazapine product page, published Dec. 6, 2012).*
Jia et al., The Journal of Pharmacology and Experimental Therapeutics vol. 349 pp. 75-84. Published online Apr. 2014.*
Wood et al., Pharmacotherapy vol. 34 pp. 89-93. Published online Aug. 2013 and presented in abstract of annual meeting of the American College of Clinical Pharmacy, Pittsburgh Pennsylvania Oct. 2011.*

(Continued)

*Primary Examiner* — Timothy P Thomas
*Assistant Examiner* — George W Kosturko
(74) *Attorney, Agent, or Firm* — McCoy Russell LLP

(57) ABSTRACT

The invention relates to the selective targeting of specific α2 adrenergic receptor subtypes for facilitating and also restoring standing and walking in a subject affected by spinal cord disorders, in particular spinal cord injury. In particular, the improvement of locomotion by targeting specific receptor subtypes can be achieved by stimulation of the α2c receptor subtype using an α2c specific agonist or by blocking the α2a receptor subtype using α2a antagonists. A combination of an α2c agonist and an α2a antagonist is also provided for a synergistic effect. Alternatively, a large α2 agonist can be used in combination with an α2a antagonist to achieve specific stimulation of the α2c receptor. Pharmaceutical compositions, kit-of-parts and therapeutic systems comprising said agonists/antagonists as active agents are objects of the present invention. A robotic interface and epidural electric stimulation can also be used in combination with the compositions of the invention for restoring voluntary control of locomotion.

8 Claims, 4 Drawing Sheets

(56) References Cited

FOREIGN PATENT DOCUMENTS

Figure 1:
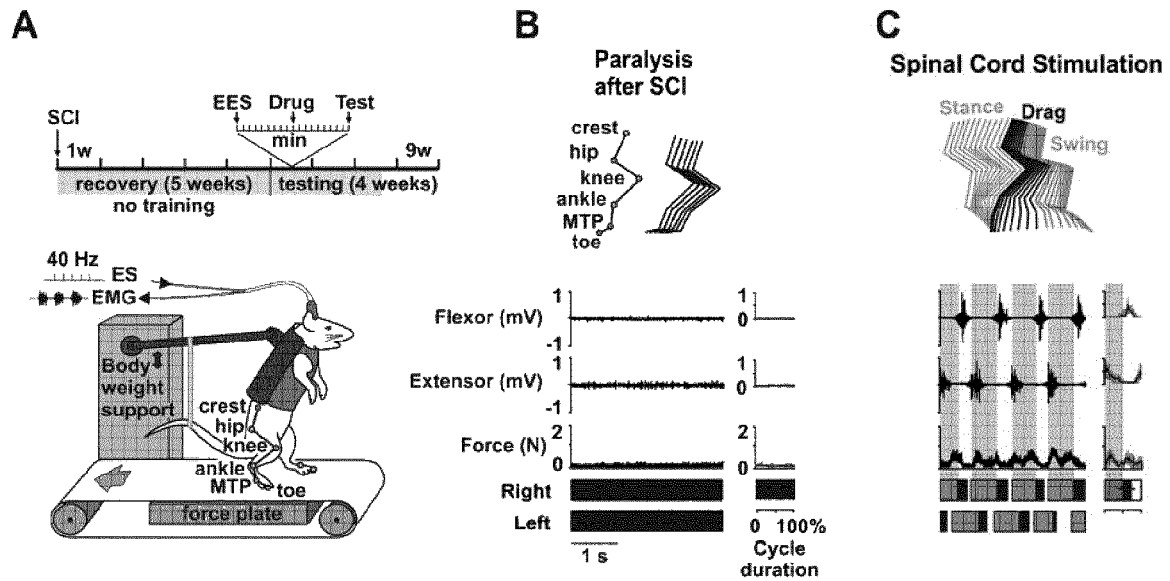

| WO | 2007047852 A2 | 4/2007 | | |
| WO | WO 2007057508 A1 * | 5/2007 | ............ | A61K 31/135 |
| WO | WO 2007057508 A2 * | 5/2007 | ............ | A61K 31/135 |
| WO | WO-2007057508 A2 * | 5/2007 | ............ | A61K 31/135 |
| WO | WO 2008092785 A1 * | 8/2008 | ............ | C07D 263/28 |

OTHER PUBLICATIONS

Paterini et al., Journal of Neuroinflammation vol. 8 pp. 1-14. Published 2011.*
Krebs-Thomas et al (Psychopharmacology vol. 189 pp. 319-329, published 2006).*
Crassous et al (J. Med. Chem. vol. 50 pp. 3964, 3968, published 2007).*
Dominici et al (Nature Medicine vol. 18, pp. 1142-1147 published online May 31, 2012).*
Paterini et al (Journal of Neuroinflannnnation vol. 8 pp. 31-45, published 2011) (Year: 2011).*
Krebs-Thomas et al (Psychopharmacology vol. 189 pp. 319-329, published 2006) (Year: 2006).*
Spinal Cord Ischemia (published 2013) (Year: 2013).*
Paterini et al (Journal of Neuroinflammation vol. 8 pp. 31-45, published 2011) (Year: 2011).*
Dominici et al (Nature Medicine vol. 18, pp. 1142-1147 published online May 31, 2012). (Year: 2012).*
Crassous et al., (J. Med Chem. vol. 50 pp. 3964-3968 published 2007) (Year: 2007).*
Paterini et al., (Journal of Neuroinflammation vol. 8 published 2011). (Year: 2011).*
Dominici et al., (Nature Medicine vol. 18 pp. 1142-1147). Published 2012. (Year: 2012).*
Jnoff et al (ChemMedChem vol. 7 pp. 385-390 published 2012). (Year: 2012).*
Int'l Search Report for PCT/EP2014/063654, six pages (dated Sep. 2014).
Written Opinion for PCT/EP2014/063654, ten pages (dated Sep. 2014).
Crassous et al. "$\alpha_2$-Adrenoreceptors profile modulation, 3.$^1$ (R)-(+)-m-nitrobiphenyline, a new efficient and $\alpha_{2C}$-subtype selective agonist" Journal of Medicinal Chemistry, vol. 50, No. 16, pp. 3964-3968 (Aug. 2007).
Delaunois et al. "Advantageous safety profile of a dual selective alpha(2C) agonist/alpha(2A) antagonist antinoceptive agent" Fundamental & Clinical Pharmacology, vol. 28, vol. 4, pp. 423-438 (Aug. 2014).
Domingo et al. "A systematic review of the effects of pharmacological agents on walking function in people with spinal cord injury" Journal of Neurotrauma, vol. 29, No. 5, pp. 865-879 (Mar. 2012).
Gad et al. "Development of a multi-electrode array for spinal cord epidural stimulation to facilitate stepping and standing after a complete spinal cord injury in adult rats" Journal of Neuroengineering and Rehabilitation, vol. 10, No. 2, 18 pages (Jan. 2013).
Genovese et al. "Selective adenosine A(2A) receptor agonists reduce the apoptosis in an experimental model of spinal cord trauma" Medline abstract only of Journal of Biological Regulators and Homeostatic Agents, vol. 24, No. 1, pp. 73-86, one page (Jan. 2010).
Genovese et al. "The selective adenosine A2A receptor agonist CGS 21680 reduces JNK MAPK activation in oligodendrocytes in injured spinal cord" Shock, vol. 32, No. 6, pp. 578-585 (Dec. 2009).
Giroux et al. "Autoradiographic study of $\alpha_1$- and $\alpha_2$-noradrenergic and serotonin1A receptors in the spinal cord of normal and chronically transected cats" Journal of Comparative Neurology, vol. 406, No. 3, pp. 402-414 (Apr. 1999).
Jnoff et al. "Discovery of selective alpha$_{2C}$ adrenergic receptor agonists" ChemMedChem, vol. 7, No. 3, pp. 385-390 (Mar. 2012).
Paterniti et al. "Selective adenosine $A_{2A}$ receptor agonists and antagonists protect against spinal cord injury through peripheral and central effects" Journal of Neuroinflammation, vol. 8, No. 31, 14 pages (Jan. 2011).
Young et al. "Novel alpha 2-adrenoceptor antagonists show selectivity for alpha 2A- and alpha 2B-adrenoceptor subtypes" European Journal of Pharmacology, vol. 168, No. 3, pp. 381-386 (Sep. 1989).
Sun, F. et al., "Sustained axon regeneration induced by co-deletion of PTEN and SOCS3," Nature, vol. 480, No. 7377, Dec. 15, 2011, Published Online Nov. 6, 2011, 12 pages.
Guyatt, G. et al., "The 6-minute walk: a new measure of exercise capacity in patients with chronic heart failure," Canadian Medical Association Journal, vol. 132, No. 8, Apr. 15, 1985, 5 pages.
Lovely, R. et al., "Effects of Training on the Recovery of Full-Weight-Bearing Stepping in the Adult Spinal Cat," Experimental Neurology, vol. 92, No. 2, May 1986, 15 pages.
Barbeau, H. et al., "Recovery of locomotion after chronic spinalization in the adult cat," Brain Research, vol. 412, No. 1, May 26, 1987, 12 pages.
Colgate, E. et al., "An Analysis of Contact Instability in Terms of Passive Physical Equivalents," Proceedings of the 1989 IEEE International Conference on Robotics and Automation, May 14, 1989, Scottsdale, Arizona, 6 pages.
Wernig, A. et al., "Laufband locomotion with body weight support improved walking in persons with severe spinal cord injuries," Paraplegia, vol. 30, No. 4, Apr. 1992, 10 pages.
Winter, D. et al., "An integrated EMG/biomechanical model of upper body balance and posture during human gait," Progress in Brain Research, vol. 97, Chapter 32, Available as Early as Jan. 1, 1993, 9 pages.
Wernig, A. et al., "Laufband Therapy Based on 'Rules of Spinal Locomotion' is Effective in Spinal Cord Injured Persons," European Journal of Neuroscience, vol. 7, No. 4, Apr. 1995, 7 pages.
Pratt, G. et al., "Stiffness Isn't Everything," Proceedings of the Fourth International Symposium on Experimental Robotics (ISER '95), Jun. 30, 1995, Stanford, California, 6 pages.
Basso, D. et al., "MASCIS Evaluation of Open Field Locomotor Scores: Effects of Experience and Teamwork on Reliability," Journal of Neurotrauma, vol. 13, No. 7, Jul. 1996, 17 pages.
Harkema, S. et al., "Human Lumbosacral Spinal Cord Interprets Loading During Stepping," Journal of Neurophysiology, vol. 77, No. 2, Feb. 1, 1997, 15 pages.
Brosamle, C. et al., "Cells of Origin, Course, and Termination Patterns of the Ventral, Uncrossed Component of the Mature Rat Corticospinal Tract," The Journal of Comparative Neurology, vol. 386, No. 2, Sep. 22, 1997, 11 pages.
Kakulas, B., "A Review of the Neuropathology of Human Spinal Cord Injury with Emphasis on Special Features," Proceedings of the Donald Munro Memorial Lecture at the American Paraplegia Society 44th Annual Conference, Sep. 9, 1998, Las Vegas, Nevada, 6 pages.
Hashtrudi-Zaad, K. et al., "On the Use of Local Force Feedback for Transparent Teleoperation," Proceedings of the 1999 IEEE International Conference on Robotics and Automation, May 10, 1999, Detroit, Michigan, 7 pages.
Kirkwood, P., "Neuronal Control of Locomotion: From Mollusc to Man—G.N. Orlovsky, T.G. Deliagina and S. Grillner. Oxford University Press, Oxford, 1999. ISBN 0198524056 (Hbk), 322 pp.," Clinical Neurophysiology, vol. 111, No. 8, Aug. 1, 2000, Published Online Jul. 17, 2000, 2 pages.
Pratt, J. et al., "Series elastic actuators for high fidelity force control," Industrial Robot: An International Journal, vol. 29, No. 3, Available as Early as Jan. 1, 2002, 13 pages.
Steward, O. et al. "False Resurrections: Distinguishing Regenerated from Spared Axons in the Injured Central Nervous System," The Journal of Comparative Neurology, vol. 459, No. 1, Apr. 21, 2003, 8 pages.
Pearson, K., "Generating the walking gait: role of sensory feedback," Progress in Brain Research, vol. 143, Chapter 12, Published Online Nov. 28, 2003, 7 pages.
Bareyre, F. et al., "The injured spinal cord spontaneously forms a new intraspinal circuit in adult rats," Nature Neuroscience, vol. 7, No. 3, Mar. 2004, Published Online Feb. 15, 2004, 9 pages.

(56) References Cited

OTHER PUBLICATIONS

Carhart, M. et al., "Epidural Spinal-Cord Stimulation Facilitates Recovery of Functional Walking Following Incomplete Spinal-Cord Injury," IEEE Transactions on Neural Systems and Rehabilitation Engineering, vol. 12, No. 1, Mar. 15, 2004, 11 pages.
Liu, J. et al., "Stimulation of the Parapyramidal Region of the Neonatal Rat Brain Stem Produces Locomotor-Like Activity Involving Spinal 5-HT7 and 5-HT2A Receptors," Journal of Neurophysiology, vol. 94, No. 2, Aug. 1, 2005, Published Online May 4, 2005, 13 pages.
Timoszyk, W. et al., "Hindlimb loading determines stepping quantity and quality following spinal cord transection," Brain Research, vol. 1050, No. 1-2, Jul. 19, 2005, Published Online Jun. 24, 2005, 10 pages.
Wernig, A., "'Ineffectiveness' of Automated Locomotor Training," Archives of Physical Medicine and Rehabilitation, vol. 86, No. 12, Dec. 2005, 2 pages.
Nessler, J. et al., "A Robotic Device for Studying Rodent Locomotion After Spinal Cord Injury," IEEE Transactions on Neural Systems and Rehabilitation Engineering, vol. 13, No. 4, Dec. 12, 2005, 10 pages.
Reinkensmeyer, D. et al., "Tools for understanding and optimizing robotic gait training," Journal of Rehabilitation Research & Development, vol. 43, No. 5, Aug. 2006, 14 pages.
Frey, M. et al., "A Novel Mechatronic Body Weight Support System," IEEE Transactions on Neural Systems and Rehabilitation Engineering, vol. 14, No. 3, Sep. 18, 2006, 11 pages.
Cai, L. et al., "Implications of Assist-As-Needed Robotic Step Training after a Complete Spinal Cord Injury on Intrinsic Strategies of Motor Learning," The Journal of Neuroscience, vol. 26, No. 41, Oct. 11, 2006, 5 pages.
Courtine, G. et al., "Can experiments in nonhuman primates expedite the translation of treatments for spinal cord injury in humans?," Nature Medicine, vol. 13, No. 5, May 2007, 13 pages.
Drew, T. et al., "Cortical mechanisms involved in visuomotor coordination during precision walking," Brain Research Reviews, vol. 57, No. 1, Jan. 2008, Published Online Aug. 22, 2007, 13 pages.
Edgerton, V. et al., "Training Locomotor Networks," Brain Research Reviews, vol. 57, No. 1, Jan. 2008, Published Online Sep. 16, 2007, 25 pages.
Kwakkel, G. et al., "Effects of Robot-assisted therapy on upper limb recovery after stroke: A Systematic Review," Neruorehabilitation and Neural Repair, vol. 22, No. 2, Mar. 2008, Published Online Sep. 17, 2007, 17 pages.
Courtine, G. et al., "Recovery of supraspinal control of stepping via indirect propriospinal relay connections after spinal cord injury," Nature Medicine, vol. 14, No. 1, Jan. 6, 2008, 6 pages.
Cowley, K et al., "Propriospinal neurons are sufficient for bulbospinal transmission of the locomotor command signal in the neonatal rat spinal cord," The Journal of Physiology, vol. 586, No. 6, Mar. 15, 2008, Published Online Jan. 31, 2008, 13 pages.
Vallery, H. et al., "Compliant Actuation of Rehabilitation Robots," IEEE Robotics & Automation Magazine, vol. 15, No. 3, Sep. 12, 2008, 10 pages.
Edgerton, V. et al., "Robotic Training and Spinal Cord Plasticity," Brain Research Bulletin, vol. 78, No. 1, Jan. 15, 2009, Published Online Nov. 14, 2008, 19 pages.
Fuentes, R. et al., "Spinal Cord Stimulation Restores Locomotion in Animal Models of Parkinson's Disease," Science, vol. 323, No. 5921, Mar. 20, 2009, 14 pages.

Musienko, P. et al., "Combinatory Electrical and Pharmacological Neuroprosthetic Interfaces to Regain Motor Function After Spinal Cord Injury," IEEE Transactions on Biomedical Engineering, vol. 56, No. 11, Nov. 2009, Published Online Jul. 24, 2009, 5 pages.
Alto, L. et al., "Chemotropic Guidance Facilitates Axonal Regeneration and Synapse Formation after Spinal Cord Injury," Nature Neuroscience, vol. 12, No. 9, Sep. 2009, Published Online Aug. 2, 2009, 22 pages.
Courtine, G. et al., "Transformation of nonfunctional spinal circuits into functional states after the loss of brain input," Nature Neuroscience, vol. 12, No. 10, Oct. 2009, Published Online Sep. 20, 2009, 12 pages.
Hägglund, M. et al., "Activation of groups of excitatory neurons in the mammalian spinal cord or hindbrain evokes locomotion," Nature Neuroscience, vol. 13, No. 2, Feb. 2010, Published Online Jan. 17, 2010, 8 pages.
Wessels, M. et al., "Body Weight-Supported Gait Training for Restoration of Walking in People With an Incomplete Spinal Cord Injury: A Systematic Review," Journal of Rehabilitation Medicine, vol. 42, No. 6, Jun. 2010, 7 pages.
Zorner, B. et al., "Profiling locomotor recovery: comprehensive quantification of impairments after CNS damage in rodents," Nature Methods, vol. 7, No. 9, Sep. 2010, Published Online Aug. 15, 2010, 11 pages.
Ada, L. et al., "Mechanically assisted walking with body weight support results in more independent walking than assisted overground walking in non-ambulatory patients early after stroke: a systematic review," Journal of Physiotherapy, vol. 56, No. 3, Sep. 2010, 9 pages.
Duschau-Wicke, A. et al., "Patient-cooperative control increases active participation of individuals with SCI during robot-aided gait training," Journal of NeuroEngineering and Rehabilitation, vol. 7, No. 43, Sep. 10, 2010, 13 pages.
Rosenzweig, E. et al., "Extensive Spontaneous Plasticity of Corticospinal Projections After Primate Spinal Cord Injury," Nature Neuroscience, vol. 13, No. 12, Dec. 2010, Published Online Nov. 14, 2010, 19 pages.
Hidler, J. et al., "ZeroG: Overground gait and balance training system," Journal of Rehabilitation Research & Development, vol. 48, No. 4, Available as Early as Jan. 1, 2011, 12 pages.
Musselman, K. et al., "Spinal Cord Injury Functional Ambulation Profile: A New Measure of Walking Ability," Neurorehabilitation and Neural Repair, vol. 25, No. 3, Mar. 2011, Published Online Feb. 25, 2011, 9 pages.
Harkema, S. et al., "Effect of Epidural stimulation of the lumbosacral spinal cord on voluntary movement, standing, and assisted stepping after motor complete paraplegia: a case study," The Lancet, vol. 377, No. 9781, Jun. 4, 2011, Published Online May 20, 2011, 17 pages.
Wirz, M. et al., "Effectiveness of automated locomotor training in patients with acute incomplete spinal cord injury: A randomized controlled multicenter trial," BMC Neurology, vol. 11, No. 60, May 27, 2011, 5 pages.
Musienko, P. et al., "Controlling specific locomotor behaviors through multidimensional monoaminergic modulation of spinal circuitries," The Journal of Neuroscience, vol. 31, No. 25, Jun. 22, 2011, 32 pages.
Musienko, P. et al. "Multi-system neurorehabilitative strategies to restore motor functions following severe spinal cord injury," Experimental Neurology, vol. 235, No. 1, May 2012, Published Online Sep. 7, 2011, 10 pages.

* cited by examiner

PHARMACOLOGICAL STIMULATION TO FACILITATE AND RESTORE STANDING AND WALKING FUNCTIONS IN SPINAL CORD MOTOR DISORDERS

This application is the U.S. national phase of International Application No. PCT/EP2014/063654, filed 27 Jun. 2014, which designated the U.S. and claims priority to EP 13174477.3, filed 1 Jul. 2013; the entire contents of each of which are hereby incorporated by reference.

The present invention relates to the field of pharmacology. In particular, it relates to the pharmacological treatment of spinal cord motor disorders through the selective targeting of α2 adrenergic receptors.

BACKGROUND OF THE INVENTION

Neuromotor disorders such as spinal cord injury (SCI) and stroke lead to distinct impairments of motor pattern generation and balance (Courtine, G., et al. Transformation of nonfunctional spinal circuits into functional states after the loss of brain input. *Nat Neurosci* 12, 1333-1342 (2009); Harkema, S. J., et al. Human lumbosacral spinal cord interprets loading during stepping. *J Neurophysiol* 77, 797-811, 1997).

A large number of studies have investigated the ability of agonists and antagonists to specific monoaminergic receptors to engage spinal locomotor networks after the interruption of descending pathways.

In particular, the function of α2 adrenergic receptors subtypes in the production of locomotion by the spinal neuronal circuitries engaged through electrical stimulation after spinal cord injury (SCI) has been investigated.

The α2 adrenergic agonist clonidine is known to induce a marked facilitation of locomotion in cats with a complete spinal cord injury (SCI) (Barbeau, Chau and Rossignol, Noradrenergic agonists and locomotor training affect locomotor recovery after cord transection in adult cats. 1993. *Brain Res Bull;* 30(3-4):387-93). Also the work of Domingo et al. (Domingo, Al-Yahya A A, Asiri Y, Eng J J, Lam T; Spinal Cord Injury Rehabilitation Evidence Research Team. A systematic review of the effects of pharmacological agents on walking function in people with spinal cord injury. J Neurotrauma. 2012 Mar. 20; 29(5):865-79. doi: 10.1089/neu.2011.2052) shows that α2 adrenergic receptor agonists clonidine and tizanidine facilitated expression of locomotion in spinalized cats.

The development of drugs engaging the α2 adrenergic system for facilitating locomotion and neurorehabilitation in humans with SCI is therefore an object of study. However, application of these pharmacological agents in humans with SCI has yielded conflicting results. For example, in human, clonidine injections dysfacilitated locomotion (Dietz V, Colombo G, Jensen L, Baumgartner L. Locomotor capacity of spinal cord in paraplegic patients. *Ann Neurol.* 1995 May; 37(5):574-82). In the same line, clonidine abolished stepping in rats with complete SCI (Controlling specific locomotor behaviors through multidimensional monoaminergic modulation of spinal circuitries. Musienko P, van den Brand R, Marzendorfer O, Roy R R, Gerasimenko Y, Edgerton V R, Courtine G. J Neuroscience 2011 Jun. 22; 31(25):9264-78).

Some works have shown that the α2 adrenergic receptor subtypes predominating in the rat spinal cord are α2a and α2c (Giroux N, Rossignol S, Reader T A. Autoradiographic study of alpha1- and alpha2-noradrenergic and serotonin1A receptors in the spinal cord of normal and chronically transected cats. J Comp Neurol. 1999 Apr. 12; 406(3):402-14; Puke M J, Luo L, Xu X J. The spinal analgesic role of alpha 2-adrenoceptor subtypes in rats after peripheral nerve section. Eur J Pharmacol. 1994 Aug. 1; 260(2-3):227-32).

However, the exact function of the different α2 receptors subtypes in the production of locomotion is still unclear. WO200203918 discloses the use of β2-agonists for recovering locomotive functions and/or neuromuscular strength following spinal cord injuries. An adrenergic receptor is targeted but different from the α2.

US2011160253 discloses deuterated Tizanidine for treating diseases and conditions that are beneficially treated by administering an α2-adrenoceptor agonist. In particular, the activity of said receptors is modulated in a cell of the central nervous system. Among the possible diseases to be cured, muscle hypertonia and muscle spasticity associated with SCI is cited. However, no specific targeting of selected adrenergic receptor subtypes is mentioned in the document and no reference is made to recovering locomotive function.

In US2011160265 an α2 receptor agonist lacking significant α-2a receptor activity is used for treating motor disorders. In particular, the α-2 receptor agonist can be an α2c receptor agonist. Spinal cord disorders, as SCI, are not listed among the motor disorders which can be treated.

In US20050059664 α-2a/α-1a selective agonists are administered for preventing or alleviating a neurological condition, where said condition can be a spinal cord trauma. However, this reference is mainly directed to the treatment of neurological pain. Locomotor activity is mentioned, but only in relation to the sedative effect of the drugs.

US2003139422 discloses use of an agonist of 5HT receptor and a β2-adrenenergic agonist for inhibiting muscular degeneration in an individual suffering from spinal cord injury.

Combinations of agonists/antagonists of specific α2 receptor subtypes have been disclosed in some patent documents, however only for applications other than neuromotor disorders.

For example, in EP2351561 it is provided a method of alleviating pain in a subject by administering to the subject a pharmaceutical composition containing an effective amount of an α-adrenergic agonist and a pharmaceutical composition containing an effective amount of a selective α-2a antagonist. Also WO2007057508 discloses the use of α2-adrenoceptor antagonists to augment the action of a μ-opioid receptor agonist for the treatment of pain, which pain can, among others, be caused by spinal cord injury or other damage of the spinal cord.

In US2009202518 a method for inhibiting an inflammatory response in a mammal comprising treating the mammal with an α2a adrenergic antagonist is disclosed.

A further example is US20060293359, wherein an α2 agonist composition is disclosed which may comprise an α2 agonist (either an α2b or 2c selective agonist or an α2 pan-agonist) having activity at the α2b and/or α2c adrenergic receptor subtypes plus comprising an additional component selected from the group consisting of an α1 receptor antagonist or an α2A receptor antagonist or both. Said composition is disclosed for treating symptoms of diabetes.

The identification of the specific α2 receptor subtypes involved in the production of locomotion as well as their specific effective targeting for the treatment of spinal cord motor disorders is still missing.

Therefore, there is still the need of a pharmacological treatment of spinal cord motor disorders in order to efficaciously improve and restore locomotion.

SUMMARY OF THE INVENTION

It has now been found that α2a and α2c adrenergic receptor subtypes play opposite roles in the control of locomotion: when stimulated, the α2a receptor has an overpowering effect and triggers a clear dysfacilitation of locomotion; on the contrary, α2c receptor stimulation triggers a clear facilitation of locomotion.

It has therefore been found that targeting specific subtypes of the α2 adrenergic receptor, instead of generally stimulate all the α2 adrenergic receptor subtypes by using an unspecific α-2 agonist, allows for a marked improvement in locomotor functions.

In particular, specifically blocking the α2a adrenergic receptor subtype provides for a clear facilitation in walking.

A similar effect is obtained by stimulating the α2c adrenergic receptor subtype.

Therefore, it is an object of the present invention a pharmaceutical composition comprising at least one molecule selectively activating α2c adrenergic receptor subtype and/or blocking α2a adrenergic receptor subtype for use for improving locomotor and postural functions, and also restoring standing and walking in a subject affected by a spinal cord motor disorder.

The combination of α2c stimulation through an α2c agonist and α2a blocking through an α2a antagonist provides for a synergistic effect, thus allowing a tremendous facilitation of locomotion.

Thus, in a preferred embodiment, the composition of the invention comprises both an α2c adrenergic receptor agonist and an α2a adrenergic receptor antagonist.

Also, the α2a adrenergic receptor antagonist can be administered in combination with an α2 receptor large agonist, for example clonidine, in order to obtain a more marked facilitation of locomotion.

Therefore, in a further embodiment of the invention said composition comprises a molecule blocking α2a adrenergic receptor subtype and a large agonist for an α2 receptor.

A kit-of-parts comprising an α2c adrenergic receptor agonist and an α2a adrenergic receptor antagonist in separate or unitary unit doses for use for improving locomotor and postural functions, and also restoring standing and walking in a subject affected by a spinal cord motor disorder is another object of the present invention.

A kit-of-parts comprising a large α2 adrenergic receptor agonist and an α2a adrenergic receptor antagonist in separate or unitary unit doses for the same use as above is also an object of the present invention.

A robotic postural neuroprosthetic interface capable of evaluating, enabling and training motor pattern generation and balance in subjects with neuromotor impairments, or any other means for rehabilitation of locomotor functions, in particular for restoring voluntary control of locomotion, can also be used together with any of the compositions of the invention for further facilitating locomotion in subjects with spinal cord disorders. In particular, the combination of pharmacological stimulation through the compositions or the kits-of parts of the invention with a robotic training and optionally also with an epidural electrical stimulation allows for the restoring of voluntary control of locomotion. All these further embodiments are objects of the present invention.

Therefore, it is also an object of the present invention a therapeutic system for restoring voluntary control of locomotion in a subject with a spinal cord disorder comprising any of the compositions or of the kits-of-parts of the invention in combination with a robotic postural neuroprosthetic interface and optionally in further combination with a device for epidural electrical stimulation.

According to the present invention, a "therapeutic system" is defined as the combination of a pharmaceutical composition, or a kit-of-parts herein disclosed with a postural neuroprosthetic interface which can optionally be combined with a device for epidural electrical stimulation. This therapeutic system is used for improving locomotor and postural functions and for restoring voluntary control of locomotion.

A method for restoring voluntary control of locomotion in a subject with a spinal cord disorder comprising the steps of:
   a. administering any of the pharmaceutical compositions or the kit-of-parts of the invention;
   b. using a robotic interface capable of evaluating, enabling and training motor pattern generation and balance;
   c. optionally providing electrical stimulation is also an object of the present invention.

DESCRIPTION OF THE INVENTION

Definitions

Within the meaning of the present invention, a spinal cord motor disorder is a disorder wherein the spinal cord is damaged and locomotor and postural functions are impaired. A spinal cord motor disorder can be caused and subsequent to trauma, infection factors (for example, extrapulmonary tuberculosis), cancer diseases, Parkinson's disease, multiple sclerosis, amyotrophy lateral sclerosis or stroke. In particular, the present invention relates to spinal cord injury.

Within the meaning of the present invention, spinal cord injury refers to any injury to the spinal cord that is caused by trauma.

Within the meaning of the present invention, an adrenergic agonist is a compound which stimulates a response from an adrenergic receptor.

Within the meaning of the present invention, an adrenergic antagonist is a compound that acts to inhibit the action of catecholamines at the adrenergic receptors.

Within the meaning of the present invention, a large agonist for the α2 receptor is an agonist to the 2a, 2b and 2c subtypes.

Within the meaning of the present invention, a kit-of-parts is an article of manufacture comprising a pharmaceutical composition comprising at least one molecule selectively activating α2c adrenergic receptor subtype and/or at least one molecule selectively blocking α2a adrenergic receptor subtype. According to the present invention, the molecule selectively activating α2c adrenergic receptor subtype and the molecule selectively blocking α2a adrenergic receptor subtype can be formulated together in a single or separate administration unit doses, suitable for concomitant, subsequent or sequential use. The kit-of-parts or the article of manufacture can be see in the form of a pharmaceutical composition.

FIGURES

FIG. 1. Experimental model. A. Timeline for the entire study and schematic representation of the experimental setup showing a spinal rat positioned bipedally in a robotically controlled supporting system. Using reflective markers overlying specific joints (MTP), a force plate located below the treadmill belt, and chronic intramuscular recording (EMG) electrodes and epidural stimulating electrodes (EES), we measured detailed kinematics, kinetics and EMG features underlying continuous hindlimb stepping on a treadmill. B-C. Representative illustrations of kinematic, kinetics and EMG features underlying spontaneous and EES-enabled locomotion recorded at 6 weeks after the lesion.

Figure 2:
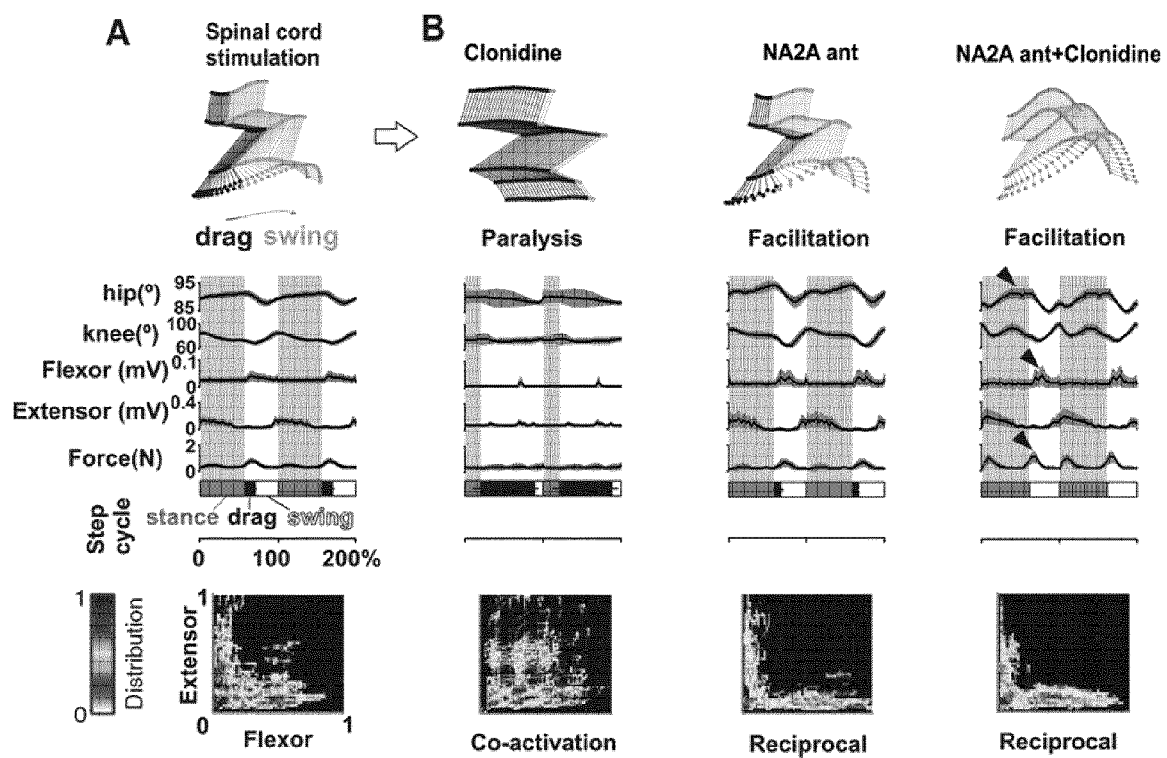

FIG. 2. Noradrenergic alpha2 receptor subtype specific modulation of stepping patterns enabled by EES in spinal rats. Representative characteristics (kinematic, EMG and kinetic) of stepping recorded during spinal cord stimulation alone (A), and after the administration of unspecific NA alpha2 agonist (clonidine) alone, specific alpha2A antagonist (BRL-44408) alone or alpha2A antagonist plus clonidine, as indicated above each panel (B). The same rat is shown in all panels.

Figure 3:
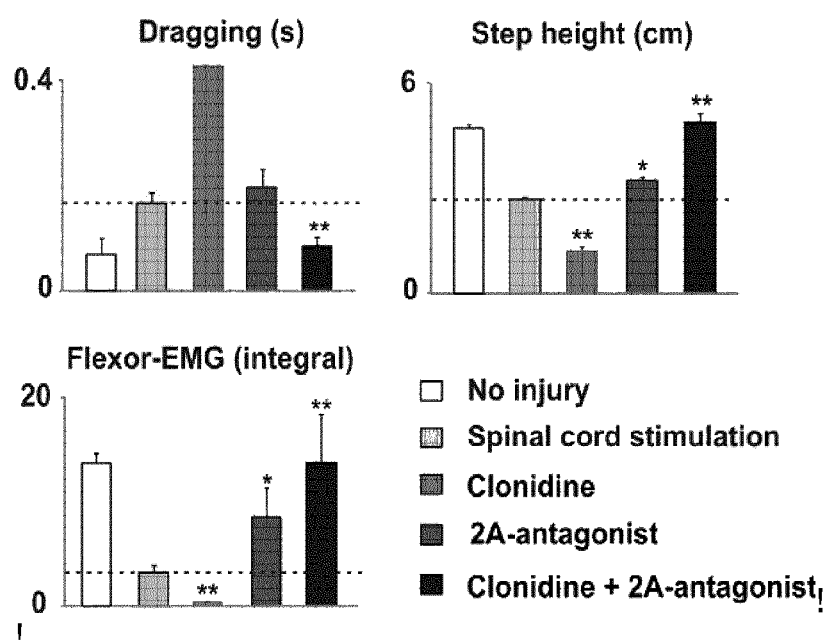

FIG. 3. Selected kinematics and EMG features of locomotor patterns. Bar graphs of average values for selected kinematics. The dotted lines represent the mean values recorded with spinal cord stimulation only.

Figure 4:
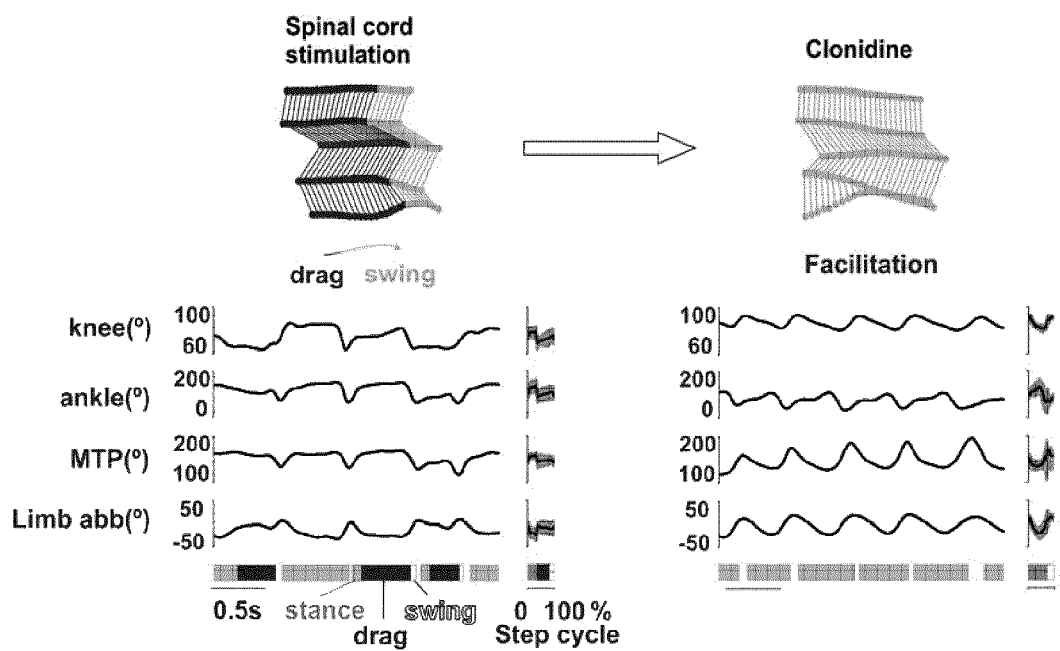
Figure 4:
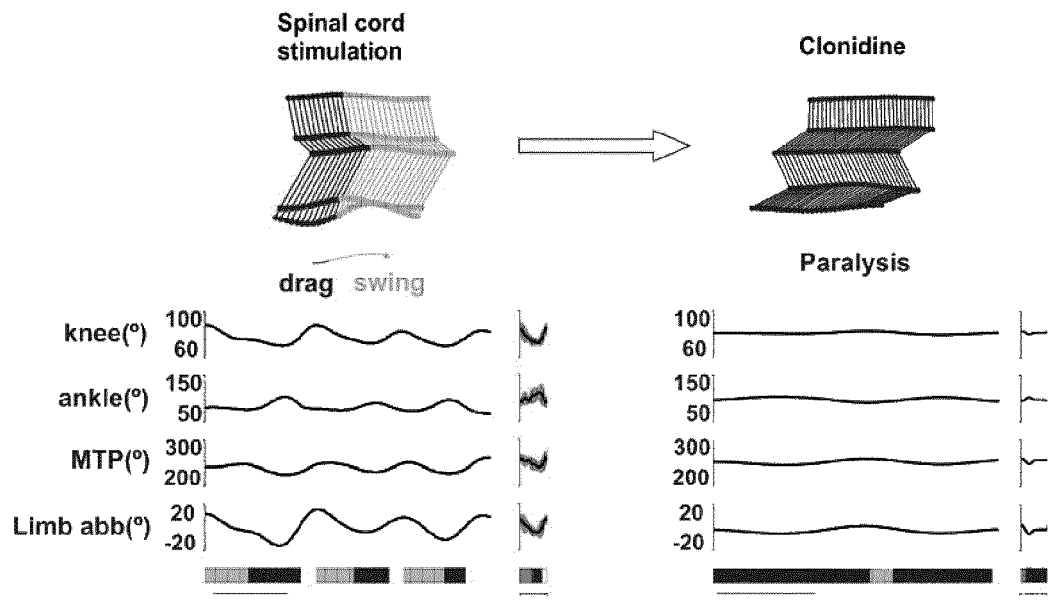

FIG. 4. Clonidine modulation of stepping patterns enabled by EES in spinal KO-mice lacking the 2a or 2c noradrenergic receptor. Representative characteristics (kinematic, EMG and kinetic) of stepping recorded during spinal cord stimulation alone and after the administration of the unspecific NA alpha2 agonist clonidine.

Figure 5:
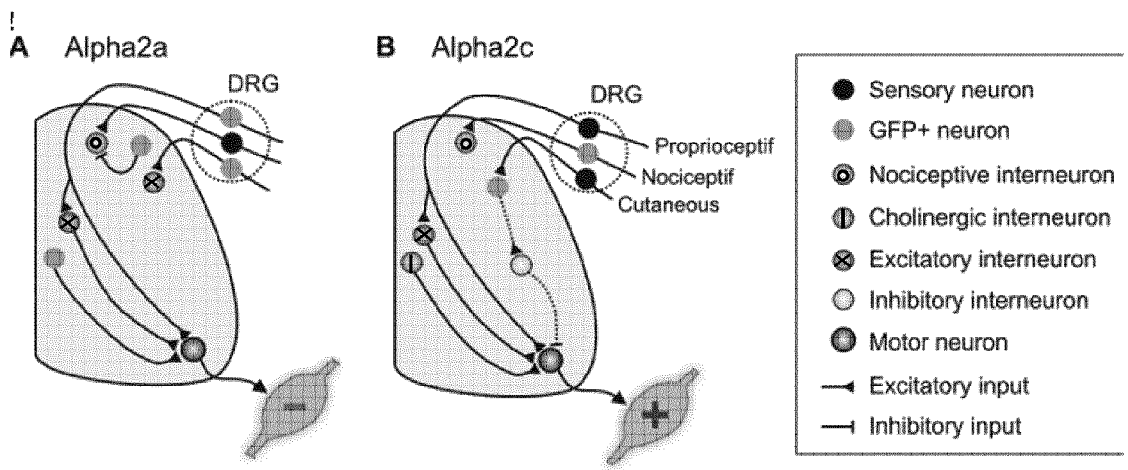

FIG. 5. Schematic summary of adrenergic receptors subtypes localization in the spinal cord and their interactions with the intraspinal circuitries.

Figure 6:
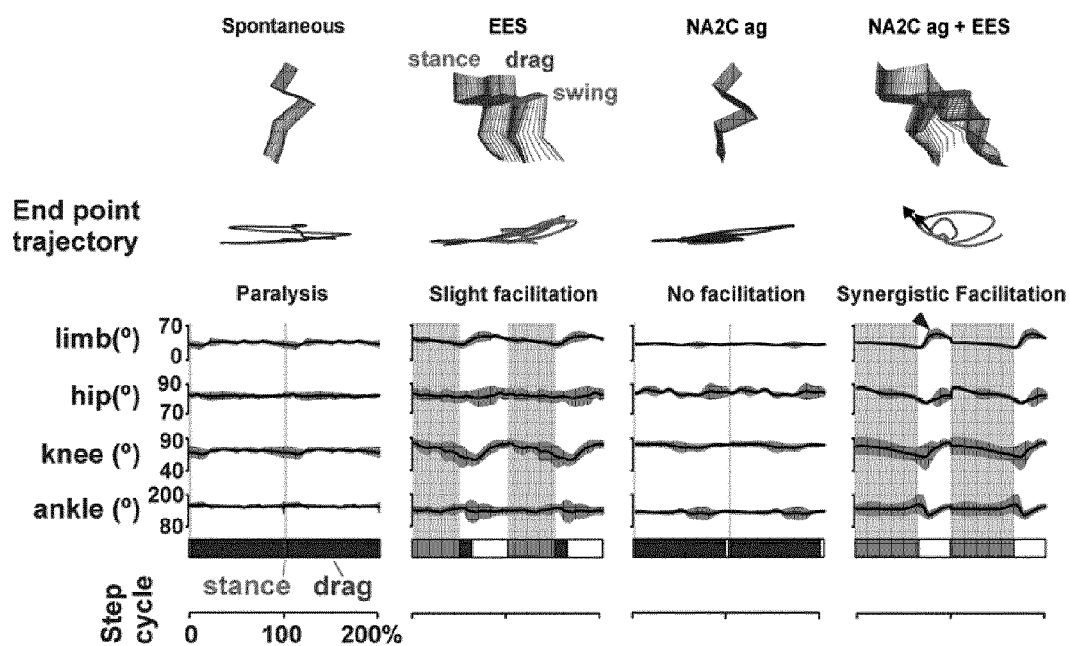

FIG. 6. Alpha2c receptor subtype specific modulation of stepping patterns enabled by EES in spinal rats. Representative characteristics of stepping patterns recorded spontaneously, during spinal cord stimulation and after the administration of a selective Alpha2c agonist alone or in combination with EES. The same rat is shown in all panels. The synergistic facilitation of locomotion when the selective alpha2c agonist is applied together with the spinal cord stimulation is shown.

DETAILED DESCRIPTION OF THE INVENTION

Alpha-2 adrenergic receptors are presently classified into three subtypes based on their pharmacological and molecular characterization: α-2a/d (α-2a in humans and α-2d in rats); α-2b; and α-2c. Alpha-2 adrenergic receptors subtypes a and c are predominantly inhibitory. The α-2a receptor subtype is predominantly expressed on myelinated proprioceptive and cutaneous afferent neurons located in dorsal root ganglions (DRG), on nociceptive inhibitory interneurons and cholinergic excitatory interneurons ("partition cells"). The α2c receptor subtype is mostly expressed on nociceptive primary afferent neurons and excitatory cutaneous interneurons.

It has been found that when stimulated by an unspecific adrenergic α2 agonist, the α2a receptor has overpowering effect and triggers a dysfacilitation of locomotion, whereas the application of a specific α2a antagonist improves locomotion.

On the contrary, it has been found that stimulation of the α2c receptor triggers a clear facilitation of stepping.

Therefore, selectively targeting (by stimulating or blocking) specific subtypes of the α2 adrenergic receptor allows for a marked improvement in locomotor functions.

In particular, blocking the α2a receptor subtype provides for a clear facilitation in walking, while a similar facilitation is obtained by stimulating the α2c receptor subtype.

Therefore, it is an object of the present invention a pharmaceutical composition comprising at least one molecule selectively activating α2c adrenergic receptor subtype and/or blocking α2a adrenergic receptor subtype for use for improving locomotor and postural functions in a subject affected by a spinal cord motor disorder.

In a preferred embodiment, said spinal cord disorder is spinal cord injury.

Furthermore, it has now been found that when the α2c receptor is stimulated by its agonist and the α2a receptor is previously or at the same time suppressed by a specific antagonist, the locomotor pattern is tremendously facilitated. The combination of the two compounds thus provides for a synergistic effect.

Therefore, in a preferred embodiment, the composition of the invention comprises both an α2c adrenergic receptor agonist and an α2a adrenergic receptor antagonist.

Also, the α2a adrenergic receptor antagonist can be administered in combination with a large agonist for an α2 receptor, for example clonidine, in order to obtain a more marked facilitation of locomotion.

Therefore, in a further embodiment of the invention said composition comprises a molecule blocking α2a adrenergic receptor subtype and a large agonist for an α2 receptor.

For improving locomotor and postural functions is intended an increase of the movements magnitudes of the hind limb joints as well as an improvement of locomotor stability. In particular, the step height and flexor muscle activity are improved and the limb dragging is reduced. Also, a better coordination of extensor and flexor activity (reciprocal) and full body weight support is achieved. Mechanistically, this improvement is related to a facilitation of the proprioceptive-associated spinal interneurons.

The present invention relates to the field of rehabilitation of subjects with impaired or totally hindered capacity of standing and walking. More in particular, the present invention relates to rehabilitation of subjects suffering from spinal cord injuries, especially lesion of the neural tissue, even complete. In turn, the aim of the present invention is to restore the communication between spinal cord and brain so to allow the subject to improve locomotor an postural functions, up to the substantially capability voluntary control of movements.

The present invention does not have the scope of alleviating pain deriving from spinal cord lesions, even though alleviation of pain could be an intrinsic effect of the administration of the pharmaceutical composition herein disclosed. The present invention is not related to the treatment of neuropathic pain.

The pharmaceutical compositions of the invention are herein referred to also as cocktails.

Alpha-adrenergic agonists are a class of sympathomimetic agents that selectively stimulates alpha-adrenergic receptors.

An α2c agonist is an agent that stimulates the α2c receptor.

An example of an agonist specific for the α2c adrenergic receptor suitable for the present invention is (R)-3-Nitrobiphenyline. (R)-3-Nitrobiphenyline is a drug which acts as an α2-adrenergic agonist, predominantly for the α2c subtype, but as well as being a weak antagonist at the α2a and α2b subtypes (Crassous P A, Cardinaletti C, Carrieri A, Bruni B, Di Vaira M, Gentili F, Ghelfi F, Giannella M, Paris H, Piergentili A, Quaglia W, Schaak S, Vesprini C, Pigini M (August 2007). "Alpha2-adrenoreceptors profile modulation. 3.1 (R)-(+)-m-nitrobiphenyline, a new efficient and alpha2C-subtype selective agonist". *Journal of Medicinal Chemistry* 50 (16): 3964-8. doi:10.1021/jm061487a. PMID.

Another example of agonist specific for the α2c adrenergic receptor suitable for the present invention is the compound of formula (I)

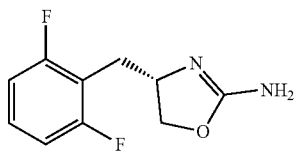

This compound is disclosed in Delaunois A, De Ron P, Dedoncker P, Rosseels M L, Cornet M, Jnoff E, Hanon E, Guyaux M, Depelchin B O; Advantageous safety profile of a dual selective alpha2C agonist/alpha2A antagonist antinociceptive agent; Fundam Clin Pharmacol. 2013 Aug. 12. doi: 10.1111/fcp.12047.

In a pharmaceutical composition comprising an α2 adrenergic receptor large agonist and an α2a adrenergic receptor antagonist, the α2 adrenergic receptor large agonist is preferably clonidine.

In a pharmaceutical composition comprising an α2a adrenergic receptor antagonist, it is preferably BRL-44408 (2-[(4,5-Dihydro-1H-imidazol-2-yl)methyl]-2,3-dihydro-1-methyl-1H-isoindole) (Novel alpha 2-adrenoceptor antagonists show selectivity for alpha 2A- and alpha 2B-adrenoceptor subtypes. Young P, Berge J, Chapman H, Cawthorne M A. Eur J Pharmacol. 1989 Sep. 22; 168(3):381-6).

A robotic postural neuroprosthetic interface capable of evaluating, enabling and training motor pattern generation and balance in subjects with neuromotor impairments, or any other means for rehabilitation of locomotor functions, in particular for restoring voluntary control of locomotion, can also be used together with any of the pharmaceutical compositions of the invention for facilitating locomotion and restoring standing and walking in subjects with spinal cord disorders. In particular, the combination of pharmacological stimulation through the compositions of the invention with a robotic training and optionally also with an epidural electrical stimulation allows for the restoring of voluntary control of locomotion.

For a description of said robotic postural neuroprosthetic interface reference can be made to the paper "Versatile robotic interface to evaluate, enable and train locomotion and balance after neuromotor disorders." Dominici N, Keller U, Vallery H, Friedli L, van den Brand R, Starkey M L, Musienko P, Nat. Med. 2012 July; 18(7):1142-7. doi: 10.1038/nm.2845.

Further reference can also be made to the paper of van den Brand R, Heutschi J, Barraud Q, DiGiovanna J, Bartholdi K, Huerlimann M, Friedli L, Vollenweider I, Moraud E M, Duis S, Dominici N, Micera S, Musienko P, Courtine G, "Restoring voluntary control of locomotion after paralyzing spinal cord injury", *Science*, 2012 Jun. 1; 336(6085):1182-5.

Therefore, it is also an object of the present invention a therapeutic system for restoring voluntary control of locomotion in a subject with a spinal cord disorder comprising any of the compositions or of the kits-of-parts of the invention in combination with a robotic postural neuroprosthetic interface and optionally in further combination with a device for epidural electrical stimulation.

The work of Gad et al. (Gad P, Choe J, Nandra M S, Zhong H, Roy R R, Tai Y C, Edgerton V R. Development of a multi-electrode array for spinal cord epidural stimulation to facilitate stepping and standing after a complete spinal cord injury in adult rats. J Neuroeng Rehabil. 2013 Jan. 21; 10:2. doi: 10.1186/1743-0003-10-2) shows the use of a multi-electrode array for spinal cord epidural stimulation to facilitate stepping and standing after a complete spinal cord injury in adult rats. To the purpose of the present invention, any suitable device for epidural stimulation can be used.

Said robotic postural neuroprosthetic interface is, for example, an automated, servocontrolled body weight support system.

It is also provided a method for restoring voluntary control of locomotion in a subject with a spinal cord disorder comprising the steps of:
a. administering any of the pharmaceutical compositions or the kit-of-parts of the invention;
b. using a robotic interface capable of evaluating, enabling and training motor pattern generation and balance;
c. optionally providing electrical stimulation.

The above steps a-c of said method can be performed simultaneously, sequentially or in any desired order.

A 5-HT1 and/or 5-HT7 serotonergic agonist can be used in combination with the active agents of the invention for facilitating and also restoring standing and walking in a subject affected by a spinal cord disorder. Preferably, said agonist is 8-OHDPAT.

8-OHDPAT is a 5-HT-1,7 agonist commonly used in experimental models such as laboratory animals, for example rat, for training, facilitating and/or restoring locomotion (Controlling specific locomotor behaviors through multidimensional monoaminergic modulation of spinal circuitries. Musienko P, van den Brand R, Marzendorfer O, Roy R R, Gerasimenko Y, Edgerton V R, Courtine G J. Neurosci. 2011 Jun. 22; 31(25):9264-78). It has been found that when 8-OHDPAT is used in combination with the α2c stimulation or the α2a blocking or both of them, a further facilitation of locomotion is observed.

Therefore, in further embodiments of the invention, the composition of the invention comprises an α2c agonist and a 5-HT1 and/or 5-HT7 serotonergic agonist or an α2a antagonist and a 5-HT1 and/or 5-HT7 serotonergic agonist or an α2c agonist and an α2a antagonist and a 5-HT1 and/or 5-HT7 serotonergic agonist or an α2 agonist and an α2a antagonist and a 5-HT1 and/or 5-HT7 serotonergic agonist. Similarly, a kit-of-parts is provided.

A method of treatment of a spinal cord disorder comprising selectively targeting an α2 adrenergic receptor subtype selected from the group consisting of α2c and α2a in a subject in need thereof is also an object of the present invention. In particular, the α2c receptor subtype can be selectively stimulated by administering a specific α2c agonist while the α2a subtype can be selectively blocked by administering an α2a antagonist. Also, a combination of an α2c agonist and an α2a antagonist can be administered. Finally, an unspecific α2 agonist can also be administered in said method of treatment in combination with a specific α2a antagonist.

The method of the invention thus provides for administration of an α2c adrenergic receptor agonist and/or an α2a adrenergic receptor antagonist to a patient with a spinal cord disorder due to an injury to the spinal cord or other conditions, leading to loss of locomotor activity, in an amount effective to treat and improve the injury or condition, in particular effective for facilitating and also restoring standing and walking. Alternatively, an unspecific α2 agonist can be administered together with an α2a antagonist. All said compositions optionally further comprise a 5-HT1 and/or 5-HT7 serotonergic agonist, preferably 8-OHDPAT.

The above method of treatments can be carried out by the compositions (or kit-of-parts) of the present invention, wherein the respective specific α2c agonist and the specific α2a antagonist can be formulated together in single dosage unit. Alternatively, said agonist and said antagonist can be formulated in respective separate dosage units. Similarly, the large α2 agonist can be formulated in the same or separate unit dose, when used together with the specific α2a antagonist. In the same manner, the 5-HT1 and/or 5-HT7 serotonergic agonist are formulated.

This allows the administration of the drugs concomitantly, or in sequential manner, according to the skilled person decision.

An effective amount is an amount which significantly improves and/or enhances locomotor function. This is readily established by a skilled practitioner based on before and after comparisons of the patient's condition using any known means.

For each active ingredient the therapeutically effective dose can be estimated initially in animal models, usually mice, rats, guinea pigs, rabbits, dogs, pigs or monkeys.

For example, suitable dosages for a composition of an α2a antagonist and an α2 agonist for rat and cat are 4-5 mg/kg of α2a antagonist i/p and 0.4 mg/kg of α2 agonist.

The animal model may also be used to determine the appropriate dose range. Such information can then be used to determine useful doses and routes for administration in humans. In calculating the Human Equivalent Dose (HED) it is recommended to use the conversion table provided by the FDA in Guidance for Industry and Reviewers (document available from FDA).

Conveniently, said compositions are in the form of a preparation for intrathecal and systemic administration, but other forms are equally suitable for carrying out the present invention. The person skilled in the art will decide the effective time of administration, depending on the patient's conditions, degree of severity of the disease, response of the patient and any other clinical parameter within the general knowledge of this matter.

A preferred administration route is injection. However, the skilled in the art can decide to administer the compositions of the invention through any suitable route.

The pharmaceutical compositions according to the present invention contain, along with the active ingredient, at least one pharmaceutically acceptable vehicle or excipient. These may be particularly useful formulation coadjuvants, e.g. solubilising agents, dispersing agents, suspension agents, and emulsifying agents.

Compositions for use in the present invention are well within the normal skill of the ordinary practitioner in the art. General knowledge is sufficient to provide any information for carrying out this aspect of the invention. Reference can be made to Remington's Pharmaceutical Sciences Handbook, last edition or any other equivalent textbook and manual.

Kit-of-parts are also provided with the present invention.

A kit-of-parts comprising an α2c adrenergic receptor agonist and an α2a adrenergic receptor antagonist in separate or unitary unit doses is a further embodiment of the present invention. Said unit doses can be administered separately, simultaneously or sequentially. In a preferred embodiment, the two compounds are administered sequentially in separate unit doses, wherein the unit comprising the α2a adrenergic receptor antagonist is administered before the unit comprising the α2c adrenergic receptor agonist.

A kit-of-parts comprising an α2 adrenergic receptor agonist and an α2a adrenergic receptor antagonist in separate or unitary unit doses is also an other embodiment of the present invention. Said unit doses can be administered separately, simultaneously or sequentially. In a preferred embodiment, the two unit doses are administered sequentially, wherein the unit comprising the α2a adrenergic receptor antagonist is administered before the unit comprising the α2 adrenergic receptor agonist.

In another embodiment the unit dose comprising the α2 agonist, for example clonidine, is administered simultaneously with the unit dose comprising the α2a antagonist, since the α2a antagonist effect is faster then the α2 agonist effect.

The kit-of parts above described can also further comprise a 5-HT1 and/or 5-HT7 serotonergic agonist, preferably 8-OHDPAT, optionally in a separate unit dose. In an embodiment, said unit dose is administered separately, simultaneously or sequentially with the unit dose comprising the α2c agonist or the α2 agonist or the α2a antagonist. In a preferred embodiment, it is administered simultaneously.

Unit-dose forms, as used herein, refers to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent.

The following examples will further illustrate the invention.

EXAMPLES

Material and Methods
Animals and Animal Care

The experiments in rats were conducted on adult female Sprague Dawley (300 g body weight). Functional testings in mice were carried out in α2a and α2c knockout animals aged 3-5 months, from both gender, obtained from L. Hein (University of Freiburg, Germany). The generation of the mouse lines lacking α2-adrenoreceptor subtypes has been previously described in detail (Abnormal regulation of the sympathetic nervous system in alpha2A-adrenergic receptor knockout mice. Altman J D, Trendelenburg A U, MacMillan L, Bernstein D, Limbird L, Starke K, Kobilka B K, Hein L. Mol Pharmacol. 1999 July; 56(1):154-61; Targeted inactivation of the gene encoding the mouse alpha 2c-adrenoceptor homolog. Link R E, Stevens M S, Kulatunga M, Scheinin M, Barsh G S, Kobilka B K. Mol Pharmacol. 1995 July; 48(1):48-55; Cardiovascular regulation in mice lacking alpha2-adrenergic receptor subtypes b and c. Link R E, Desai K, Hein L, Stevens M E, Chruscinski A, Bernstein D, Barsh G S, Kobilka B K. Science. 1996 Aug. 9; 273(5276): 803-5). To investigate the spinal distribution of the α2 subtypes, we used BAC transgenic mice expressing the reporter protein GFP upstream the coding sequence of the α2a or α2c receptor subtype (strains 014248-UCD and 030098-UCD MMRRC, USA). All procedures were approved by the Veterinary Office of the Canton of Vaud, Switzerland. Animals were housed individually on a 12 h light/dark cycle, with access to food and water ad libitum.

Surgical Procedures and Postsurgical Care

All procedures have been described in detail previously (see above, Courtine et al., 2009). Briefly, under general anesthesia and aseptic conditions, a partial laminectomy was performed over spinal segments L2 and S1. Teflon-coated stainless-steel wires (AS632; Cooner Wire) were passed under the spinous processes and above the dura mater of the remaining vertebrae between the partial laminectomy sites.

Bipolar intramuscular EMG electrodes using the same wire type as above were inserted bilaterally in the midbelly of the tibialis anterior (TA), midbelly of the vastus lateralis (VL), distal deep compartment of the semitendinosus (St), and medial deep region of the medial gastrocnemius (MG) muscles. All electrode wires were connected to a percutaneous amphenol connector cemented to the rat skull. In the same surgical intervention, the spinal cord was transected completely at a midthoracic level (T7) (Courtine et al., 2009).

Testing Protocols

All tested animals were allowed to recover for 2-5 weeks after lesion to regain stable levels of excitability in the spinal networks to facilitate locomotion via EES (Epidural stimulation induced modulation of spinal locomotor networks in adult spinal rats. Lavrov I, Dy C J, Fong A J, Gerasimenko Y, Courtine G, Zhong H, Roy R R, Edgerton V R. J Neurosci. 2008). An upper body harness was used to position the rats over a treadmill belt and to partially support their body weight during bipedal locomotion (FIG. 1A). An automated, servocontrolled body weight support system (Robomedica) measured and provided the optimal amount of body weight support that each rat needed to step. To facilitate locomotion via EES, monopolar rectangular pulses (0.2 ms duration) were delivered at 40 Hz using two constant-current stimulators (AM Systems) connected to the electrodes positioned at L2 and S1. The stimulation was delivered between the active electrode (L2 or S1) and an indifferent ground located subcutaneously on the lateral aspect of the body. The frequency and intensity of stimulation was adjusted (40 Hz, 0.2 ms, 50-200 µA) to obtain optimal facilitation of stepping visually. All experimental testing followed the same protocol.

Experimental Groups

Experimental recordings were conducted in rats and KO mice in which the contribution of the noradrenergic receptors subtypes 2a and 2c to the modulation of gait patterns were investigated thoroughly.

The animals were tested every other day for several weeks, (FIG. 1A). Each testing session consisted of a series of 10-20 steps first with spontaneous locomotion and then with EES alone, followed (10 min later) by a series of 10-20 steps with or without EES under a given pharmacological agent (FIG. 1A).

Pharmacological Interventions

We used the α2a antagonist BRL-44408 (4.5 mg/kg, Sigma-Aldrich) and the α2 non-specific agonist clonidine (0.4 mg/kg, Sigma-Aldrich). In rat experiments, the drugs were sequentially injected into the intraperitoneal space: BRL-44408 was delivered first followed 5 minutes later by clonidine. In KO mice experiments, only clonidine was injected intraperitoneally.

Kinematics, Kinetics, and EMG Recordings-Kinematics.

Three-dimensional video recordings (200 Hz) were made using the motion capture system VICON. Eight infrared television cameras (200 Hz) were used to track the motion of reflective markers attached bilaterally at the iliac crest, greater trochanter, lateral condyle, lateral malleolus, distal end of the fifth metatarsal [metatarsophalangeal joint (MTP)], and tip of the toe (FIG. 1A). Nexus (Vicon) was used to obtain 3-D coordinates of the markers. The body was modeled as an interconnected chain of rigid segments, and joint angles were generated accordingly.

Kinetics.

Moments and ground reaction forces in the vertical, antero-posterior, and mediolateral directions were monitored using a biomechanical force plate (2 kHz; HE6X6; AMTI) located below the treadmill belt (FIG. 1A). Vicon BodyBuilder (Vicon) was used to compute the displacements of the center of foot pressures.

EMG.

EMG signals (2 kHz) were amplified, filtered (10-1000 Hz bandpass), stored, and analyzed off-line to compute the amplitude, duration, and timing of individual bursts (Courtine et al., 2009).

Data Analyses

Ten successive step cycles were extracted for both the left and right hindlimbs from a continuous sequence of stepping on the treadmill for each animal under each condition. When no stepping movements were observed, a 10 s period was recorded and analyzed. A total of 129 parameters quantifying gait, kinematics, kinetics, and EMG features were computed for each limb and gait cycle according to methods described in detail previously (Kinematic and EMG determinants in quadrupedal locomotion of a non-human primate (Rhesus). Courtine G, Roy R R, Hodgson J, McKay H, Raven J, Zhong H, Yang H, Tuszynski M H, Edgerton V R. J Neurophysiol. 2005 June; 93(6):3127-45; Recovery of supraspinal control of stepping via indirect propriospinal relay connections after spinal cord injury. Courtine G, Song B, Roy R R, Zhong H, Herrmann J E, Ao Y, Qi J, Edgerton V R, Sofroniew M V. Nat Med. 2008 January; 14(1):69-74; Transformation of nonfunctional spinal circuits into functional states after the loss of brain input. Courtine G, Gerasimenko Y, van den Brand R, Yew A, Musienko P, Zhong H, Song B, Ao Y, Ichiyama R M, Lavrov I, Roy R R, Sofroniew M V, Edgerton V R. Nat Neurosci. 2009 October; 12(10): 1333-42).

These parameters provided a holistic quantification of locomotor patterns ranging from general features of gait to fine details of limb motions and coordination. To allow direct comparisons between the different experimental conditions, all computed variables were normalized to those measured before drug injection (i.e., during locomotion facilitated by dual-site EES alone).

Statistical Analyses

The pharmacological agents used in this study promoted substantial modulations of gait patterns, which were evident in the modification of a large proportion of the 129 computed parameters. To evaluate the more important and reproducible modulation patterns mediated by the different drugs across rats, we established a new, multistep statistical procedure based on principal component (PC) analysis (Courtine et al., 2009). PCs were extracted and a PC score along each axis was computed to quantify differences between conditions. In the vast majority of cases, PC1 differentiated locomotion under EES (baseline) or EES plus antagonist drugs versus locomotion under EES plus agonists to the tested receptor.

Considering the large number of parameters computed, we only reported the variables that showed the largest factor loadings across all experimental conditions, for both single and combinatory testing. All data are reported as mean values±SEM. Repeated-measures ANOVAs were used to test differences between locomotor parameters recorded before and after drug injections Example 1

Alpha2 Receptor Subtypes Specific Modulation of Stepping Patterns Enabled by EES in Spinal Rats Experiments were conducted on adult animals that received a complete midthoracic (T7) spinal cord transection which permanently removed all supraspinal input below the level of the lesion. To reach stable levels of excitability in the spinal networks to facilitate stepping electrically (Lavrov et al., 2008), the rats were allowed to recover for 5 weeks after lesion before initiating experimental recordings (FIG. 1A). At this time point and during the subsequent 4 weeks after lesion, the rats showed no (FIG. 1B) spontaneous hindlimb stepping when supported in a bipedal posture on a moving treadmill belt (13 cm/s) (FIG. 1A). In contrast, continuous (40 Hz, 0.2 ms, 50-200 µA) EES applied dorsally over the S1 and L2 spinal segments generated continuous hindlimb locomotion on the treadmill in all rats tested (FIGS. 1C and 2A).

A marked facilitation of locomotion by the α2 adrenergic agonist clonidine has been demonstrated repeatedly in spinal cats (On the central generation of locomotion in the low spinal cat. Grillner S, Zangger P. Exp Brain Res. 1979; Effects of intrathecal alpha1- and alpha2-noradrenergic agonists and norepinephrine on locomotion in chronic spinal cats. Chau C, Barbeau H, Rossignol S. J Neurophysiol. 1998 June; 79(6):2941-63). In sharp contrast with an enhancement of stepping ability in spinal cats, the α2 agonist clonidine (0.4-0.5 mg/kg) abolished the stepping enabled by EES in spinal rats (FIG. 2B). Activation of all the α2 receptors subtypes transformed continuous patterns of locomotion into gait patterns ranging from hopping to complete paralysis (FIG. 2B). As a consequence, a large number of gait parameters changed significantly (FIG. 3), generally showing a suppression of locomotor function after administering clonidine in spinal rats. Low clonidine dosages were also shown to suppress or markedly reduce locomotor EMG activity in humans with a severe spinal cord injury (Dietz et al., 1995).

The α2a antagonist BRL-44408 (4-5 mg/kg) conversely improved locomotion (FIG. 2B), modulating various parameters in opposite directions compared with clonidine (FIG. 3). Blocking α2a receptors reduced paw dragging (FIG. 3) and substantially improved the step height.

Moreover, a tremendous facilitation of locomotion has been observed when the combination of α2a antagonist and clonidine (activation of α2c receptor) is applied together with the spinal cord stimulation (FIG. 2B). This combination significantly improved the step height and flexor muscle activity and reduced the paw dragging. The grey-shaded plots in FIG. 2 (density distribution) illustrated better coordination of extensor and flexor activity (reciprocal) during stepping after BRL-44408 and clonidine injections.

In total, a significant facilitation of the locomotor characteristics can be observed when the α2a antagonist is applied alone and even more in combination with clonidine.

Example 2

Blocking of the α2a and α2c Noradrenergic Receptors in Knockout (KO) Mice

To validate the results obtained with a pharmacological blocking of the α2A and α2C noradrenergic receptors we performed supplementary experiments in knockout (KO) mice. Electrical epidural stimulation was applied as described in Example 1. Two groups of spinal mice lacking α2a or α2c receptors were injected with clonidine, a non specific agonist of the alpha 2 receptor subtypes (FIG. 4). In the α2a KO mice, clonidine injection triggered a facilitation of the locomotor function, an increase of the movement magnitudes of the hindlimb joints as well as an improvement of locomotor stability (FIG. 4A). Conversely, clonidine injection in α2c KO mice resulted in a significant blocking of the locomotor abilities of the animal (FIG. 4B).

Alpha 2 receptors subtypes a and c are predominantly inhibitory. The α2a receptor subtype is predominantly expressed on myelinated proprioceptive and cutaneous afferent neurons located in dorsal root ganglions (DRG), on nociceptive inhibitory interneurons and cholinergic excitatory interneurons. When stimulated by the unspecific NA α2 agonist (Clonidine), the α2a receptor has overpowering effect and triggers a dysfacilitation of locomotion. On the other hand, the application of the specific 2a antagonist (BRL-44408) moderately improves locomotion. The α2c receptor subtype is mostly expressed on nociceptive primary afferent neurons and excitatory cutaneous interneurons. When stimulated, α2c receptors by its agonist (Clonidine) and previously suppressed the α2a receptors by BRL-44408, the locomotor pattern is tremendously facilitated.

Morphological analyses conducted on transgenic mice expressing the reporter gene EGFP immediately upstream of the coding DNA sequence of α2a or α2c uncovered the mechanisms involved in the production of locomotion following the various agonist injections. They show that the α2a receptor subtype is predominantly expressed on proprioceptive and cutaneous afferent neurons located in dorsal root ganglions, on nociceptive inhibitory interneurons and cholinergic excitatory interneurons ("partition cells") (FIG. 5A). When stimulated by the unspecific α2 agonist (Clonidine), the α2a receptor has overpowering effect and triggers a dysfacilitation of locomotion. Conversely, the α2c subtype is mostly expressed on nociceptive primary afferent neurons and excitatory cutaneous interneurons (FIG. 5B). When stimulated α2a receptors by its agonist (Clonidine) and previously suppressed the α2a receptor activity by BRL-44408, the locomotor pattern is tremendously facilitated.

Taken together, the neurophysiologic and histological experiments have shown that α2a and α2c noradrenergic receptors subtypes are distributed on counteracting neuronal pathways and play opposite roles in the control of locomotor functions. Stimulation of the α2a subtype significantly impaired the spinal locomotor network whereas α2c receptor activation had a clearly facilitating effect. Simultaneous suppression of the α2a receptors by BRL-44408 and α2c receptors activation by Clonidine remarkably recovered the locomotor function in the previously paralyzed mice, rats and cats.

Example 3

Alpha2c Receptor Subtype Specific Stimulation Facilitates Stepping Patterns Enabled by EES in Spinal Rats Experiments were conducted on adult animals that received a complete midthoracic (T7) spinal cord transection which permanently removed all supraspinal input below the level of the lesion. To reach stable levels of excitability in the spinal networks to facilitate stepping electrically (Lavrov et al., 2008), the rats were allowed to recover for 2 weeks after lesion before initiating experimental recordings (FIG. 6). At this time point, the rats showed no spontaneous hindlimb stepping when supported in a bipedal posture on a moving treadmill belt (13 cm/s). In contrast, continuous (40 Hz, 0.2 ms, 50-200 µA) EES applied dorsally over the S1 and L2 spinal segments generated continuous hindlimb locomotion on the treadmill in all rats tested (FIG. 6).

The α2c agonist, a 2-amino-oxazoline derivative of formula (I) ($C10N2H10OF2$, 200 umol/kg), significantly improved locomotion (FIG. 2B), exclusively when applied together with the spinal cord stimulation (FIG. 6). This combination increased the limb amplitude and reduced the paw dragging.

The invention claimed is:

1. A method for improving motor functions in a subject affected by a spinal cord injury, comprising a step of selectively targeting α2 adrenergic receptor subtypes selected from the group of α2c and α2a via administering a pharmaceutical composition comprising at least one molecule activating an α2c adrenergic receptor subtype and at least one molecule blocking an α2a adrenergic receptor subtype to the subject, wherein the at least one molecule activating the α2c adrenergic receptor subtype does not include a non-specific α2 agonist, to improve the motor functions of the subject, wherein said at least one molecule activating the α2c adrenergic receptor subtype is selected from the group consisting of (R)-3-Nitrobiphenyline and a compound of formula (I);

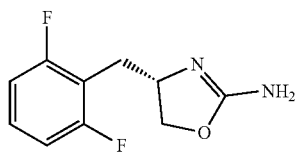 [SMILES: NC1=N[C@@H](Cc2c(F)cccc2F)CO1]

(I)

wherein improving the motor functions in the subject includes facilitating locomotion in the subject, the method further comprising a step of using a robotic interface capable of evaluating, enabling, and training motor pattern generation and balance to restore voluntary control of locomotion in the subject; and wherein the foregoing steps are performed simultaneously, sequentially, or in any desired order.

2. The method according to claim 1, wherein the at least one molecule blocking an α2a adrenergic receptor subtype to the subject is an α2a antagonist BRL-44408.

3. The method according to claim 1, wherein said composition further comprises a 5-HT1 and/or 5-HT7 serotonergic agonist.

4. The method according to claim 1, wherein said composition is in injectable form.

5. The method according to claim 1, further comprising a step of providing epidural electrical stimulation;
wherein the foregoing steps are performed simultaneously, sequentially, or in any desired order.

6. The method according to claim 1, wherein facilitating locomotion in the subject includes facilitating stepping.

7. The method according to claim 1, wherein the spinal cord injury includes an impaired or totally hindered capacity of standing and walking.

8. The method according to claim 1, wherein the step of selectively targeting α2 adrenergic receptor subtypes and the step of using a robotic interface are initiated after a recovery period of 2-5 weeks after the spinal cord injury.

* * * * *